United States Patent
Olesen et al.

(10) Patent No.: US 7,645,791 B2
(45) Date of Patent: Jan. 12, 2010

(54) SALICYLIC ANILIDES

(75) Inventors: Preben Houlberg Olesen, Copenhagen (DK); Thomas Kruse Hansen, Herlev (DK); Lise Brown Christiansen, Lyngby (DK); Holger Claus Hansen, Væløse (DK)

(73) Assignee: High Point Pharmaceuticals, LLC, High Point, NC (US)

( * ) Notice: Subject to any disclaimer, the term of this patent is extended or adjusted under 35 U.S.C. 154(b) by 0 days.

(21) Appl. No.: 12/147,678

(22) Filed: Jun. 27, 2008

(65) Prior Publication Data

US 2009/0005434 A1   Jan. 1, 2009

Related U.S. Application Data

(63) Continuation of application No. 11/440,938, filed on May 25, 2006, now abandoned, which is a continuation of application No. PCT/DK2004/000304, filed on May 4, 2004.

(60) Provisional application No. 60/526,378, filed on Dec. 1, 2003.

(30) Foreign Application Priority Data

Nov. 25, 2003   (DK) ............................... 2003 01738

(51) Int. Cl.
- *A61K 31/36*   (2006.01)
- *A61K 31/343*  (2006.01)
- *A61K 31/381*  (2006.01)
- *C07D 317/70*  (2006.01)
- *C07D 333/76*  (2006.01)
- *C07D 409/08*  (2006.01)

(52) U.S. Cl. ........................ 514/443; 514/463; 514/468; 549/44; 549/52; 549/433

(58) Field of Classification Search .................. 514/443, 514/463, 468; 549/44, 52, 433; 546/290
See application file for complete search history.

(56) References Cited

U.S. PATENT DOCUMENTS

| | | | |
|---|---|---|---|
| 4,025,647 | A | 5/1977 | Eakin et al. |
| 4,673,691 | A | 6/1987 | Bachynsky |

FOREIGN PATENT DOCUMENTS

| | | |
|---|---|---|
| DE | 034102 | 3/1952 |
| DE | 834102 * | 3/1952 |
| EP | 322823 | 4/1995 |
| FR | 1513274 | 2/1968 |
| GB | 728098 | 4/1955 |
| GB | 1493375 | 11/1977 |
| JP | 2000086677 | 3/2000 |
| WO | WO 97/24116 | 7/1997 |
| WO | WO 00/06143 | 2/2000 |
| WO | WO 01/07028 | 2/2001 |
| WO | WO 01/44172 | 6/2001 |
| WO | WO 01/82924 | 11/2001 |
| WO | WO 01/96944 | 12/2001 |
| WO | WO03103648 | 6/2003 |
| WO | WO03103655 | 6/2003 |
| WO | WO 2004/041256 | 5/2004 |

OTHER PUBLICATIONS

Brown, G.R. et al., J. Med. Chem., vol. 28, pp. 143-146 (1985).
De Grey, A.D.N.J., Eur J. Biochem., vol. 269, p. 1995 (2002).
Marcielag, M.J. et al., J. Med. Chem., vol. 41, pp. 2939-2949 (1998).
Miyoshi, H. et al., Biochem. Biophys. ACTA, vol. 891, pp. 293-299 (1987).
Terada, H. et al., Biochem. Biophys. ACTA, vol. 936, pp. 504-512 (1988).
International Search Report completed Aug. 24, 2004.
Weidner, M.A. "Amidino Benzimidazole Inhibitors of Bacterial Two-Component Systems," *Bioorganic & Medicinal Chemistry Letters*, 2001, vol. 11, pp. 1545-1548.

* cited by examiner

*Primary Examiner*—Taofiq A Solola
(74) *Attorney, Agent, or Firm*—Samuel B. Rollins

(57) ABSTRACT

Novel salicylic anilides are chemical uncouplers useful e.g. for the treatment of obesity.

17 Claims, No Drawings

SALICYLIC ANILIDES

CROSS-REFERENCE TO RELATED APPLICATIONS

This application is a continuation of U.S. application Ser. No. 11/440,938, filed May 25, 2006, which is a continuation of International Application Number: PCT/DK2004/000304, filed May 4, 2004, which claims priority to Danish Patent Application Number PA 2003 01738, filed Nov. 25, 2003, and U.S. Provisional Application No. 60/526,378, filed Dec. 1, 2003, the contents of each of which is incorporated herein in its entirety.

FIELD OF THE INVENTION

The present invention relates to novel salicylic anilide derivatives. The derivatives are effective chemical uncouplers, and are thus useful in the treatment of e.g. obesity.

BACKGROUND OF THE INVENTION

Obesity is a well-known risk factor for the development of many very common diseases such as atherosclerosis, hypertension, type 2 diabetes (non-insulin dependent diabetes mellitus (NIDDM)), dyslipidemia, coronary heart disease, and osteoarthritis and various malignancies. It also causes considerable problems through reduced motility and decreased quality of life. The incidence of obese people and thereby also these diseases is increasing throughout the entire industrialised world.

The term obesity implies an excess of adipose tissue. In this context obesity is best viewed as any degree of excess adiposity that imparts a health risk. The cut off between normal and obese individuals can only be approximated, but the health risk imparted by the obesity is probably a continuum with increasing adiposity. In the context of the present invention, individuals with a body mass index (BMI=body weight in kilograms divided by the square of the height in meters) above 25 are to be regarded as obese Even mild obesity increases the risk for premature death and conditions such as diabetes, dyslipidemia, hypertension, atherosclerosis, gallbladder disease and certain types of cancer. In the industrialised western world the prevalence of obesity has increased significantly in the past few decades. Because of the high prevalence of obesity and its health consequences, its prevention and treatment should be a high public health priority.

Except for exercise, diet and food restriction, which is not feasible for a vast number of patients, no convincing treatment for reducing body weight effectively and acceptably currently exist. However, not only in view of the considerable problems directly related to obesity as described above, but also due to the important effect of obesity as a risk factor in serious and even mortal and common diseases, it is important to find pharmaceutical compounds which are useful in prevention and/or treatment of obesity.

When energy intake exceeds expenditure, the excess calories are stored predominately in adipose tissue, and if this net positive balance is prolonged, obesity results, i.e. there are two components to weight balance, and an abnormality on either side (intake or expenditure) can lead to obesity. This process may be counteracted by increasing the energy expenditure (for instance via exercise) or decreasing the energy intake (for instance by dieting). Pharmacological treatment available up to date only consists of Sibutramine (acting via serotonergic mechanisms, Abbott) and Orlistat (reducing fat uptake from the gut, Roche Pharm) neither reducing body weight effectively nor acceptably. There is therefore a need for pharmaceutical compounds which may be useful in prevention and/or treatment of obesity, for instance by increasing the energy expenditure or decreasing the energy intake.

One way of increasing energy expenditure is by increasing the metabolic rate. Oxidative phosphorylation in mitochondria, the energy from glucose metabolism and free fatty acids oxidation is used to drive the phosphorylation of ADP to ATP. When NADH and $FADH_2$ formed in the TCA cycle are oxidised back to $NAD^+$ and FAD respectively, protons are pumped out of the mitochondrial matrix. The resulting pH gradient (matrix pH~8 and outside pH~7) and potential (~−170 mV, inside negative) across the inner mitochondrial membrane constitute the electrochemical proton gradient. As the effect of a one-unit pH difference corresponds to a potential of 61.5 mV, the electrochemical proton gradient exerts a proton-motive force of roughly −230 mV, which is the driving force for the mitochondrial ATP synthesis.

When the ATP consumption thus increases, the cells respond by increasing the ATP synthesis and consequently the inward flux of protons through the ATP synthase, the enzyme responsible for ATP synthesis and thereby the metabolic rate is increased. Chemical uncouplers are compounds, which can transport protons across membranes, and when protons are transported across the inner mitochondrial membrane, the ATP synthase is bypassed. At the (alkaline) matrix side the proton is released and the deprotonated uncoupler returns to the inter-membrane space where it picks up another proton. The cycling of the uncoupler (or ATP synthesis) and the resulting proton transport leads to an increased outward pumping of protons through an increased oxidation of NADH and $FADH_2$ by the respiration chain. The NADH concentration in the matrix will consequently drop. Since NADH feedback inhibits three steps in the TCA cycle (NADH is the main regulator of the TCA cycle), the flux through the TCA cycle will increase. Hence, the metabolic rate will increase.

Compounds, such as chemical uncouplers, which act by increasing the metabolic rate may thus be useful for treating obesity, but also for treating other conditions such as atherosclerosis, hypertension, diabetes, especially type 2 diabetes (NIDDM (non-insulin dependent diabetes mellitus)), dyslipidemia, coronary heart disease, gallbladder disease, osteoarthritis and various types of cancer such as endometrial, breast, prostate and colon cancers and the risk for premature death as well as other conditions, such as diseases and disorders, which conditions are improved by a reduced mitochondrial potential.

Furthermore, chemical uncouplers may reduce reactive oxygen species (ROS) that are assumed (De Grey et al, Eur J. Biochem 269, 1995 ff (2002)) to be involved in the aging process, in damage of heart tissue as well as neuronal tissue. It is therefore also possible that conditions affected by ROS may be reversed or halted by intervention by chemical uncouplers. Examples of such conditions include diabetic microvascular diseases in the retina, renal glomerulus and peripheral nerves cell.

The best known chemical uncoupler is 2,4-dinitrophenol (DNP), which has been shown to increase energy expenditure in humans as well as animals. The side effects at higher doses include increased perspiration, vasodilatation, skin rashes, cataracts, neuritis and death! Two fatalities amongst the first 100.000 persons treated with DNP, and the fact that the lowest dose, which could be lethal, was only twice the average dose giving a desired 50% increase in basal metabolic rate giving a very narrow safety window combined with other factors led to the removal of DNP from the market. Since then nobody have attempted to develop or market uncouplers for the treatment of obesity.

DNP is the best known chemical uncoupler; but many other compounds are known to induce uncoupling. DNP derivatives such as 4,6-dinitro-o-cresol (Victoria Yellow) and 2,4-dinitro-1-naphtol (Martius Yellow) as well as structurally unrelated compounds such as 2,6-dit-butyl-4-(2',2'-dicyanovinyl)phenol) (SF6847) (also known as 2-(3,5-di-tert-butyl-4-hydroxy-benzylidene)-malononitrile), carbonylcyanide m-chlorophenylhydrazone (CCCP) and carbonylcyanide ptrifluoromethoxy-phenylhydrazone (FCCP) (Miyoshi H et al. Quantitative relationship between protenophoric and uncoupling activities of analogs of SF6847 (2,6-di-t-butyl-4-(2',2'-dicyanovinyl)phenol), Biochimica et Biophysica Acta 891, 293-299 (1987)) are uncouplers.

Another class of chemical uncouplers is the salicylanilides of which S-13 is the most potent compound discovered so far (Terada H et al. Structural Requirements of Salicylanilides for Uncoupling Activity in Mitochondria Quantitative Analysis of Structure—Uncoupling Relationships, Biochimica et Biophysica Acta 936, 504-512 (1988)).

WO00/06143 to Texas Pharmaceuticals Inc. relates to a method for inducing intracellular hyperthermia comprising a step of administering a mitochondrial uncoupling agent, such as 2,4-dinitrophenol.

U.S. Pat. No. 4,673,691 to Bachynsky relates to the use of 2,4-dinitrophenol for treating obesity.

Various salisylic anilide derivatives have been disclosed in the literature. As an example, U.S. Pat. No. 4,025,647 discloses compounds of the formula

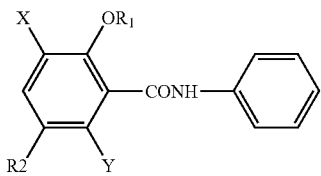

wherein R1 may be hydrogen, X is secondary or tertiary alkyl, R2 alkanoyl, phenylsulfinyl, phenylsulfonyl, etc, and Y is hydrogen or methyl. The compounds have anthelmintic activity, especially against liver fluke.

EP 322823 discloses electrophotographic photoreceptors with the following formula

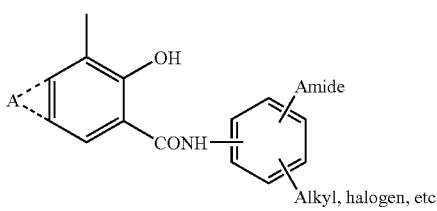

wherein A is a group of atoms necessary to condense the benzene ring with another ring.

WO 01/44172 discloses compounds of the formula

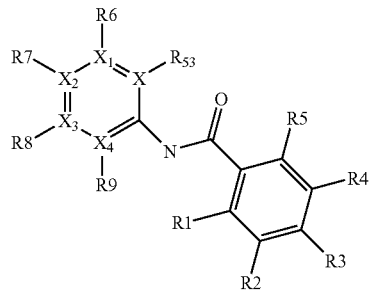

wherein all X's may be carbon, R1 may be hydroxyl, R2-R5 may be optionally substituted aryl heteroaryl, alkylaryl, alkyl, ester, amide, etc. The compounds are inhibitors of serine proteases, urokinase, Factor Xa, Factor VIIa and have utility as anticancer agents and as anticoagulants. R7 is amidine or guadinyl for all compounds specifically disclosed in this application.

WO 01/96944 discloses compounds of the formula

wherein R represent 0-4 substituents selected from alkyl, aryl, aralkyl, etc. The compounds are useful as components in colour photothermographic films. None of the specifically disclosed compounds have a branched alkyl or phenyl as substituent in the left-most phenyl ring.

WO 01/82924 discloses compounds of the formula

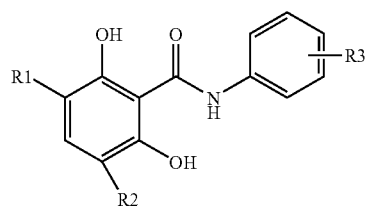

wherein R1-3 represents hydrogen, alkyl, halo, alkoxy, etc. The compounds are phosphate transport inhibitors.

SUMMARY OF THE INVENTION

The present inventors have surprisingly found that salicylic anilides of formula I are potent chemical uncouplers. Accordingly, the present invention relates to compounds according to formula I

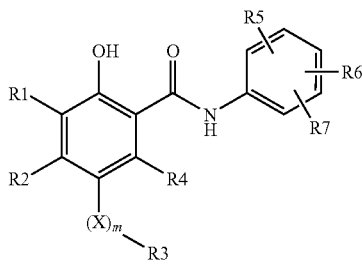

wherein X represent

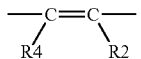

or —C≡C—, and m is 0, 1 or 2;

R1 represents branched $C_{1-6}$alkyl or phenyl;

R2 and R4 independently represent, hydrogen, $C_{1-6}$alkyl, $C_{1-6}$alkenyl, $C_{1-6}$alkynyl or $C_{1-6}$alkoxy;

R5, R6 and R7 independently represent hydrogen, nitro, cyano, halogen, —OR8, $C_{1-6}$haloalkoxy, $C_{1-6}$haloalkyl, $C_{1-6}$alkyl, —C(O)OR8, —COR8, —C(O)NR8R8, —SH, —S(O)2OR8, —S(O)$_2$N(R8)$_2$, —S(O)$_n$R9, aryl, heteroaryl, wherein said aryl and heteroaryl may optionally be substituted with one or more $C_{1-6}$alkyl, oxo or phenyl wherein said phenyl is substituted with one or more halogen or $C_{1-6}$ alkyl; n is 0, 1, 2 and each R8 independently represents hydrogen or $C_{1-6}$alkyl, and R9 represents $C_{1-6}$alkyl;

R3 represents $C_{1-6}$alkyl, $C_{1-6}$alkenyl, $C_{1-6}$alkynyl, $C_{1-6}$haloalkyl, aryl$C_{1-6}$alkyl, aryl$C_{1-6}$alkenyl, aryl$C_{1-6}$alkynyl, heteroaryl$C_{1-6}$alkyl, heteroaryl$C_{1-6}$alkenyl, heteroaryl$C_{1-6}$alkynyl, $C_{3-8}$cycloalkyl, aryl, or heteroaryl; wherein R3 may optionally be substituted with up to four substituents, R10, R11, R12, and R13, wherein R10, R11, R12, and R13 independently represent $C_{1-6}$alkyl, $C_{1-6}$alkylaryl, halogen, $C_{1-6}$haloalkyl, $C_{1-6}$hydroxyalkyl, $C_{1-6}$alkoxy, oxo, cyano, nitro, —(CH2)$_r$OR14, —SH, —S(O)$_p$R15, —S(O)$_p$N (R14)(R15), —C(O)OR14, —OC(O)R14, —C(O)R14, —C(O)N(R14)(R15), —(CH2)$_r$N(R14)C(O)R15-, —B(OR14)(OR15), —(CH2)$_r$N(R14)(R15), or phenyl, wherein said phenyl is optionally substituted with one or more substituents selected from the group consisting of $C_{1-6}$alkyl, halogen, $C_{1-6}$haloalkyl, $C_{1-6}$hydroxyalkyl, cyano, nitro, —OR16-, —S(O)$_s$R16, —C(O)OR16, —OC(O)R16, —C(O)R16, —C(O)N(R16)(R17), —N(R16)(R17), —(CH$_2$)$_s$N(R16)C(O)R17, —B(OR16)(OR17)-, —(CH2)$_t$OR16, or —(CH$_2$)$_t$N(R16)(R17);

each R14 independently represents hydrogen, $C_{1-6}$haloalkyl, $C_{1-6}$hydroxyalkyl, $C_{1-6}$alkyl, $C_{1-6}$alkenyl, $C_{1-6}$alkynyl, $C_{3-8}$cycloalkyl, or phenyl optionally substituted with one or more substituents selected from the group consisting of $C_{1-6}$alkyl, halogen, $C_{1-6}$haloalkyl, $C_{1-6}$hydroxyalkyl and cyano;

R15 represents $C_{1-6}$haloalkyl, $C_{1-6}$hydroxyalkyl, $C_{1-6}$alkyl, $C_{1-6}$alkenyl, $C_{1-6}$alkynyl, $C_{3-8}$cycloalkyl, or phenyl optionally substituted with one or more substituents selected from the group consisting of $C_{1-6}$alkyl, halogen, $C_{1-6}$haloalkyl, $C_{1-6}$hydroxyalkyl and cyano; or wherein R14 and R15, when attached to a nitrogen atom, together with said nitrogen atom form a $C_{3-8}$cycloalkyl or heteroaryl ring, optionally substituted with one or more $C_{1-6}$alkyl substituents;

each R16 and R17 independently represents hydrogen, $C_{1-6}$haloalkyl, $C_{1-6}$hydroxyalkyl, $C_{1-6}$alkyl, $C_{1-6}$alkenyl, $C_{1-6}$alkynyl or $C_{3-8}$cycloalkyl; or R16 and R17, when attached to a nitrogen atom, together with said nitrogen atom form a cycloalkyl or heteroaryl ring, optionally substituted with one or more alkyl substituents;

p and s, independently of each other, are an integer of 0, 1, or 2;

r and t, independently of each other, are an integer of 0, 1, 2, or 3;

q is 0, 1, 2;

provided that the compound is not N-(2-chloro-4-nitrophenyl)-3-tert-butyl-6-methylsalicylanilide, 3,5-Di-tert-butyl-N-(2-chloro-4-nitro-phenyl)-2-hydroxy-benzamide or 3-tert-Butyl-N-(2-chloro-4-nitro-phenyl)-2-hydroxy-5-methyl-benzamide;

and pharmaceutically acceptable salts, solvates and prodrugs thereof.

The present invention also relates to the use of compounds of formula I in therapy, and in particular to pharmaceutical compositions comprising said compounds.

In another aspect, the invention relates to therapeutic methods comprising administering a therapeutically effective amount of a compound of formula I to a patient in need thereof.

In a still further aspect, the invention relates to the use of compounds of formula I in the manufacture of medicaments.

DEFINITIONS

In the present context, the term "alkyl" is intended to indicate a straight or branched chain saturated monovalent hydrocarbon radical having from one to twelve carbon atoms, also denoted as $C_{1-12}$-alkyl. Typical alkyl groups are alkyl groups with from one to eight or from one to six carbon atoms, also denoted as $C_{1-8}$-alkyl and $C_{1-6}$-alkyl respectively. Typical $C_{1-6}$-alkyl groups include, but are not limited to e.g. methyl, ethyl, n-propyl, isopropyl, n-butyl, sec-butyl, isobutyl, tert-butyl, n-pentyl, 2-methylbutyl, 3-methylbutyl, 4-methylpentyl, n-pentyl, n-hexyl, 1,1-dimethylpropyl, 1,2-dimethylpropyl, 2,2-dimethylpropyl (neopentyl), 1,2,2-trimethylpropyl and the like, while typical $C_{1-8}$-alkyl groups include the same groups as well as alkyl groups having seven or eight carbon atoms, such as heptyl, octyl, 2,2-dimethylhexyl and the like. The term "$C_{1-6}$-alkyl" as used herein also includes secondary $C_{3-6}$-alkyl and tertiary $C_{4-6}$-alkyl. The term "$C_{1-8}$-alkyl" as used herein also includes secondary $C_{3-8}$-alkyl and tertiary $C_{4-8}$-alkyl. The term "$C_{1-12}$-alkyl" as used herein also includes secondary $C_{3-12}$-alkyl and tertiary $C_{4-12}$-alkyl.

In the present context, the term "alkenyl" is intended to indicate a straight or branched chain monovalent hydrocarbon radical having from two to six carbon atoms and at least one carbon-carbon double bond, for example $C_{3-5}$-alkenyl. Typical $C_{3-5}$-alkenyl groups include vinyl, allyl, 1-propenyl, 1,3 butadiene-1-yl, and the like. The term "conjugated alkenyl" as used herein, alone or in combination, refers to an alkenyl having consecutive double bonds, such as for instance 1,3 butadiene-1-yl.

In the present context, the term "alkynyl" is intended to indicate a straight or branched chain monovalent hydrocarbon radical having from two to six carbon atoms and at least one carbon-carbon triple bond and optionally one or more carbon-carbon double bonds. Examples include ethynyl, propynyl and 3,4-pentadiene-1-ynyl.

The term "halogen" is intended to indicate members of the seventh main group of the periodic system, i,e, fluoro, chloro, bromo and iodo.

In the present context, the term "aryl" is intended to indicate a carbocyclic aromatic ring radical which may optionally be fused to another ring, which may be aromatic or non-aromatic, aromatic or non-aromatic. Typical aryl groups include phenyl, biphenylyl, indenyl, fluorene, naphthyl (1-naphthyl, 2-naphthyl), anthracenyl (1-anthracenyl, 2-anthracenyl, 3-anthracenyl), 1,2,3,4-tetrahydro quinolyl, 1,2,3, 4-tetrahydro naphthyl, and the like.

The term "heteroaryl", as used herein, alone or in combination, refers to an aromatic ring radical with for instance 5 to 7 member atoms, or to a fused aromatic ring system radical with for instance from 7 to 18 member atoms, wherein at least on ring is aromatic, containing one or more heteroatoms selected from nitrogen, oxygen, or sulfur heteroatoms, wherein N-oxides and sulfur monoxides and sulfur dioxides are permissible heteroaromatic substitutions. Examples include furanyl, thienyl, thiophenyl, pyrrolyl, imidazolyl, pyrazolyl, triazolyl, tetrazolyl, thiazolyl, oxazolyl, isoxazolyl, oxadiazolyl, thiadiazolyl, isothiazolyl, pyridinyl, pyridazinyl, pyrazinyl, pyrimidinyl, quinolinyl, isoquinolinyl, benzofuranyl, benzothiophenyl, indolyl, and indazolyl, thienyl (2-thienyl, 3-thienyl), furanyl (2-furanyl, 3-furanyl), indolyl, oxadiazolyl, isoxazolyl, thiadiazolyl, oxatriazolyl, thiatriazolyl, quinazolinyl, fluorenyl, xanthenyl, isoindanyl, benzhydryl, acridinyl, thiazolyl, pyrrolyl (1-pyrrolyl, 2-pyrrolyl, 3-pyrrolyl), pyrazolyl (1-pyrazolyl, 3-pyrazolyl, 4-pyrazolyl, 5-pyrazolyl), imidazolyl (1-imidazolyl, 2-imidazolyl, 4-imidazolyl, 5-imidazolyl), triazolyl (1,2,3-triazol-1-yl, 1,2,3-triazol-4-yl 1,2,3-triazol-5-yl, 1,2,4-triazol-3-yl, 1,2,4-triazol-5-yl), oxazolyl (2-oxazolyl, 4-oxazolyl, 5-oxazolyl), isoxazolyl (isoxazo-3-yl, isoxazo-4-yl, isoxaz-5-yl), isothiazolyl (isothiazo-3-yl, isothiazo-4-yl, isothiaz-5-yl) thiazolyl (2-thiazolyl, 4-thiazolyl, 5-thiazolyl), pyridinyl (2-pyridinyl, 3-pyridinyl, 4-pyridinyl), pyrimidinyl (2-pyrimidinyl, 4-pyrimidinyl, 5-pyrimidinyl, 6-pyrimidinyl), pyrazinyl, pyridazinyl (3-pyridazinyl, 4-pyridazinyl, 5-pyridazinyl), quinolinyl (2-quinolinyl, 3-quinolinyl, 4-quinolinyl, 5-quinolinyl, 6-quinolinyl, 7-quinolinyl, 8-quinolinyl), isoquinolinyl (1-isoquinolinyl, 3-isoquinolinyl, 4-isoquinolinyl, 5-isoquinolinyl, 6-isoquinolinyl, 7-isoquinolinyl, 8-isoquinolinyl), benzo[b]furanyl (2-benzo[b]furanyl, 3-benzo[b]furanyl, 4-benzo[b]furanyl, 5-benzo[b]furanyl, 6-benzo[b]furanyl, 7-benzo[b]furanyl), 2,3-dihydrobenzo[b]furanyl (2-(2,3-dihydro-benzo[b]furanyl), 3-(2,3-dihydro-benzo[b]furanyl), 4-(2,3-dihydro-benzo[b]furanyl), 5-(2,3-dihydro-benzo[b]furanyl), 6-(2,3-dihydro-benzo[b]furanyl), 7-(2,3-dihydro-benzo[b]furanyl)), benzo[b]thiophenyl (benzo[b]thiophen-2-yl, benzo[b]thiophen-3-yl, benzo[b]thiophen-4-yl, benzo[b]thiophen-5-yl, benzo[b]thiophen-6-yl, benzo[b]thiophen-7-yl), 2,3-dihydro-benzo[b]thiophenyl (2,3-dihydro-benzo[b]thiophen-2-yl, 2,3-dihydrobenzo[b]thiophen-3-yl, 2,3-dihydro-benzo[b]thiophen-4-yl, 2,3-dihydro-benzo[b]thiophen-5-yl, 2,3-dihydro-benzo[b]thiophen-6-yl, 2,3-dihydro-benzo[b]thiophen-7-yl), indolyl (1-indolyl, 2-indolyl, 3-indolyl, 4-indolyl, 5-indolyl, 6-indolyl, 7-indolyl), indazolyl (1-indazolyl, 3-indazolyl, 4-indazolyl, 5-indazolyl, 6-indazolyl, 7-indazolyl), benzimidazolyl (1-benzimidazolyl, 2-benzimidazolyl, 4-benzimidazolyl, 5-benzimidazolyl, 6-benzimidazolyl, 7-benzimidazolyl, 8-benzimidazolyl), benzoxazolyl (2-benzoxazolyl, 3-benzoxazolyl, 4-benzoxazolyl, 5-benzoxazolyl, 6-benzoxazolyl, 7-benzoxazolyl), benzothiazolyl (2-benzothiazolyl, 4-benzothiazolyl, 5-benzothiazolyl, 6-benzothiazolyl, 7-benzothiazolyl), carbazolyl (1-carbazolyl, 2-carbazolyl, 3-carbazolyl, 4-carbazolyl), 5H-dibenz[b,f]azepinyl (5H-dibenz[b,f]azepin-1-yl, 5H-dibenz[b,f]azepine-2-yl, 5H-dibenz[b,f]azepine-3-yl, 5H-dibenz[b,f]azepine-4-yl, 5H-dibenz[b,f]azepine-5-yl), 10,11-dihydro-5H-dibenz[b,f]azepinyl (10, 11-dihydro-5H-dibenz[b,f]azepine-1-yl, 10,11-dihydro-5H-dibenz[b,f]azepine-2-yl, 10,11-dihydro-5H-dibenz[b,f]azepine-3-yl, 10,11-dihydro-5H-dibenz[b,f]azepine-4-yl, 10,11-dihydro-5H-dibenz[b,f]azepine-5-yl), benzo[1,3]dioxole (2-benzo[1,3]dioxole, 4-benzo[1,3]dioxole, 5-benzo[1,3]dioxole, 6-benzo[1,3]dioxole, 7-benzo[1,3]dioxole), and tetrazolyl (5-tetrazolyl, N-tetrazolyl).

A "fused ring system" as used herein, alone or in combination, refers to a carbocyclic or heterocyclic ring radical fused to another carbocyclic or heterocyclic ring radical, the two rings having two atoms in common. Typical fused aromatic ring systems include, but are not limited to napthalene, quinoline, isoquinoline, indole, and isoindole.

In the present context the term "cycloalkyl" is intended to indicate a cyclic saturated monovalent hydrocarbon radical having 3, 4, 5, 6, 7 or 8 ring carbon atoms.

In the present context, the term "alkoxy" is intended to indicate a radical of the formula —OR', wherein R' represents alkyl as indicated above.

The term "haloalkoxy" is intended to indicate an alkoxy as defined above substituted with one or more halogen, such as fluoro, chloro, bromo or iodo.

In the present context, the term "alkylamino" is intended to indicate a radical of the formula —NH—R' or —N(R')$_2$, wherein each R' represents alkyl as indicated above.

The term "nitro" shall mean the radical —NO$_2$.

The term "cyano" shall mean the radical —CN.

In the present context, the term "haloalkyl" is intended to indicate an alkyl, as defined above, substituted with one or more halogens, as defined above. Examples include trihalomethyl, such as trifluoromethyl and trichloromethyl, and 2,2,2-trichloro-1-ethyl.

In the present context, the term "hydroxyalkyl" is intended to indicate an alkyl, as defined above, substituted with one or more hydroxyl groups. Examples include hydroxymethyl, 1-hydroxy-1-ethyl and 2-hydroxy-1-ethyl.

As used herein, the term "solvate" is a complex of defined stoichiometry formed by a solute (in casu, a compound according to the present invention) and a solvent. Solvents may be, by way of example, water, ethanol, or acetic acid.

As used herein, the term "prodrug" includes biohydrolyzable amides and biohydrolyzable esters and also encompasses a) compounds in which the biohydrolyzable functionality in such a prodrug is encompassed in the compound according to the present invention, and b) compounds which may be oxidized or reduced biologically at a given functional group to yield drug substances according to the present invention. Examples of these functional groups include 1,4-dihydropyridine, N-alkylcarbonyl-1,4-dihydropyridine, 1,4-cyclohexadiene, tert-butyl, and the like.

In the present context, the term "pharmaceutically acceptable salt" is intended to indicate salts which are not harmful to the patient. Such salts include pharmaceutically acceptable acid addition salts, pharmaceutically acceptable metal salts, ammonium and alkylated ammonium salts. Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, paminobenzoic, glutamic, benzenesulfonic, p-toluenesulfonic acids and the like. Further examples of pharmaceutically acceptable inorganic or organic acid addition salts include the pharmaceutically acceptable salts listed in J. Pharm. Sci. 1977, 66, 2, which is incorporated herein by reference. Examples of metal salts include lithium, sodium, potassium, magnesium salts and the like. Examples of ammonium and alkylated ammonium salts include ammonium, methylammonium, dimethylammonium, trimethylammonium, ethylammonium, hydroxyethylammonium, diethylammonium, butylammonium, tetramethylammonium salts and the like.

A "therapeutically effective amount" of a compound as used herein means an amount sufficient to cure, alleviate or partially arrest the clinical manifestations of a given disease and its complications. An amount adequate to accomplish this is defined as "therapeutically effective amount". Effective amounts for each purpose will depend on the severity of the disease or injury as well as the weight and general state of the subject. It will be understood that determining an appropriate dosage may be achieved using routine experimentation, by constructing a matrix of values and testing different points in the matrix, which is all within the ordinary skills of a trained physician or veterinary.

The term "treatment" and "treating" as used herein means the management and care of a patient for the purpose of combating a condition, such as a disease or a disorder. The term is intended to include the full spectrum of treatments for a given condition from which the patient is suffering, such as administration of the active compound to alleviate the symptoms or complications, to delay the progression of the disease, disorder or condition, to alleviate or relief the symptoms and complications, and/or to cure or eliminate the disease, disorder or condition as well as to prevent the condition, wherein prevention is to be understood as the management and care of a patient for the purpose of combating the disease, condition, or disorder and includes the administration of the active compounds to prevent the onset of the symptoms or complications. The patient to be treated is preferably a mammal, in particular a human being, but it may also include animals, such as dogs, cats, cows, sheep and pigs.

DESCRIPTION OF THE INVENTION

In one embodiment, m is 0. In another embodiment, m is 1, and in still another embodiment, m is 2.

In one embodiment, R1 represents phenyl, neopentyl, tert-butyl, isopropyl or 1,1-dimethylpropyl, and in particular tert-butyl In one embodiment, R2 and R4 independently represent hydrogen or methyl.

In one embodiment, R3 represents $C_{1-6}$alkenyl or $C_{1-6}$alkynyl, both of which are optionally substituted. Particular examples of R3 include styryl.

In one embodiment, R3 represents optionally substituted aryl. Particular examples of R3 include phenyl, 4-chloro phenyl, 4-nitro phenyl, 4-trifluoromethyl phenyl, 4-cyano phenyl, or radicals with the following structures

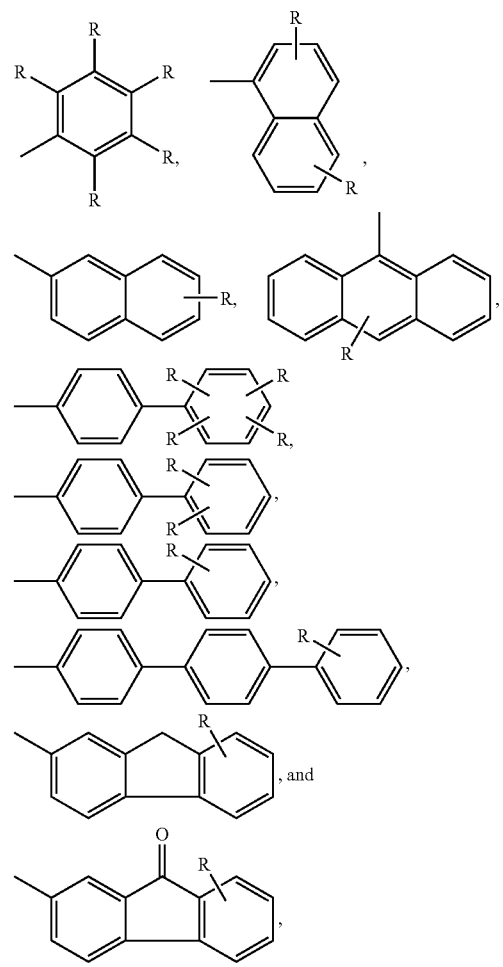

wherein R is selected from the list consisting of hydrogen, methyl, $CF_3$, Cl, Br, F, methoxy, ethoxy, methylcarbonyl, nitro, cyano, and phenyl, wherein said phenyl may optionally be substituted with Cl, Br, F, $CF_3$ or methoxy. Particular examples of R3 include phenyl and 4-cyano phenyl.

In another embodiment, R3 represents an optionally substituted heteroaryl. Particularly, R3 may be selected from

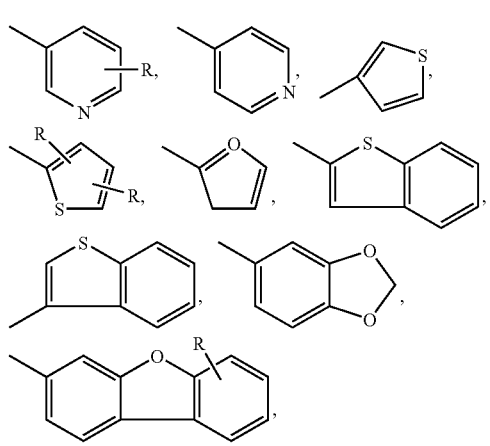

-continued

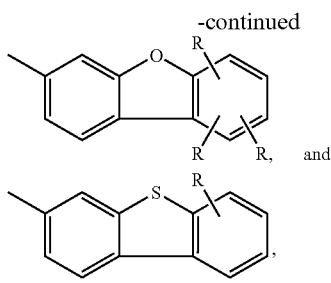

wherein R is selected from the list consisting of hydrogen, methyl, CF₃, Cl, Br, F, methoxy, ethoxy, methylcarbonyl, nitro, cyano, and phenyl, wherein said phenyl may optionally be substituted with Cl, Br, F, CF₃ or methoxy. Particular mentioning is made of thiophe-2-yl, 5-cyano-thiophen-2-yl and benzo[b]thiophen-2-yl.

In another embodiment, one or more of R5, R6 and R7 are selected from nitro, cyano, halogen, haloalkyl, haloalkoxy, optionally substituted alkyl or optionally substituted heteroaryl. In particular, R5, R6 and R7 may together constitute the following substitution patterns 2-chloro-4-nitro; 2-trifluoromethoxy-4-nitro; 4-(1-imidazolyl); 2-trifluoromethyl-4-(1-imidazolyl); and 2-methyl-4-(1-imidazolyl). Particular mentioning is made of 2-chloro-4-nitro and 2-trifluoromethoxy-4-nitro.

In one embodiment, the compound of formula I is selected from the list consisting of
5-tert-Butyl-4-hydroxy-2-methyl-biphenyl-3-carboxylic acid (2-chloro-4-nitro-phenyl)-amide;
E) 3-tert-Butyl-N-(2-chloro-4-cyano-phenyl)-2-hydroxy-5-styryl-benzamide;
5-tert-Butyl-4-hydroxy-2-methyl-biphenyl-3-carboxylic acid (4-cyano-2-trifluoromethoxyphenyl)-amide;
5-tert-Butyl-4'-cyano-4-hydroxy-2-methyl-biphenyl-3-carboxylic acid (4-cyano-2-trifluoromethoxy-phenyl)-amide;
3-tert-Butyl-N-(2-chloro-4-cyano-phenyl)-5-(5-cyano-thiophen-2-yl)-2-hydroxy-benzamide; and
5-Benzo[b]thiophen-2-yl-3-tert-butyl-N-(2-chloro-4-cyano-phenyl)-2-hydroxy-benzamide.

Compounds according to formula I may comprise chiral carbon atoms or carbon-carbon double bonds which may give rise to stereo isomeric forms, e.g. enantiomers, diastereomers and geometric isomers. The present invention relates to all such isomers, either in pure form or as mixtures thereof. Pure isomeric forms may either be prepared from intermediates which are pure isomers themselves, by purification of a mixture of isomers after the synthesis, or by a combination of the two methods. Purification of isomeric forms are well-known in the art, e.g. as described by Jaques in Enantiomers, Racemates and Resolution, Wiley, 1981.

The compounds of the present invention are useful in the treatment of diseases or states that benefit from an increase in the mitochondrial respiration.

The compounds of the present invention are believed to be particular well-suited for the treatment of obesity as such or preventing weight gain and for the treatment of diseases or disorders where obesity is involved in the etiology. In one embodiment, the invention thus provides a method of treating the metabolic syndrome, insulin resistance, dyslipidemia, hypertension, obesity, type 2 diabetes, type 1 diabetes, diabetic late complications including cardiovascular diseases, cardiovascular disorders, disorders of lipid metabolism, neurodegenerative and psychiatric disorders, dysregulation of intraocular pressure including glaucoma, atherosclerosis, hypertension, coronary heart disease, gallbladder disease, osteoarthritis, and cancer.

More specifically such conditions include the metabolic syndrome, type 2 diabetes (especially in obese patients), diabetes as a consequence of obesity, insulin resistance, hyperglycemia, prandial hyperglycemia, hyperinsulinemia, impaired glucose tolerance (IGT), impaired fasting glucose (IFG), increased hepatic glucose production, type 1 diabetes, LADA, pediatric diabetes, dyslipidemia (especially in obese patients), diabetic dyslipidemia, hyperlipidemia, hypertriglyceridemia, hyperlipoproteinemia, micro-/macroalbuminuria, nephropathy, retinopathy, neuropathy, diabetic ulcers, cardiovascular diseases, arteriosclerosis, coronary artery disease, cardiac hypertrophy, myocardial ischemia, heart insufficiency, congestive heart failure, stroke, myocardial infarction, arrythmia, decreased blood flow, erectile dysfunction (male or female), myopathy, loss of muscle tissue, muscle wasting, muscle catabolism, osteoporosis, decreased linear growth, neurodegenerative and psychiatric disorders, Alzheimers disease, neuronal death, impaired cognitive function, depression, anxiety, eating disorders, appetite regulation, migraine, epilepsy, addiction to chemical substances, disorders of intraocular pressure, bacterial infections, mycobacterial infections. In the present context cancer is intended to include forms such as hematological cancer, such as leukemia, acute myeloide leukemia, chronic myeloide leukemia, chronic lymphatic leukemia, myelodysplasia, multiple myeloma, Hodgkin's disease, or solid tumor forms, such as fibrosarcom, small or non-small cell long carcinoma, gastric, intestinal or colorectal cancer, prostate, endometrial, ovarian or breast cancer, brain, head or neck cancer, cancer in the urinary tract, such as kidney or bladder cancer, malignant melanoma, liver cancer, uterine and pancreatic cancer.

In another embodiment, the invention relates to the use of a chemical uncoupler according to the present invention for maintaining a weight loss.

Use of the compounds according to the present invention in the treatment of obesity may very likely reduce or eliminate the side effects such as irritation of the skin, glaucoma etc. known from treatment of obesity with DNP and other chemical uncouplers with narrow safety windows.

Uncouplers may also reduce insulin release from β-cells and may thus be useful in providing β-cell rest. Inducing β-cell rest may be useful in connection with β-cell transplantation, and it has also been described that inducing β-cell rest may be useful in preventing diabetes.

Obesity drugs which regulate the appetite and reduce food intake often suffer from lack of long-term efficiency in terms of body weight loss because the body in response to the treatment lowers the rate of the metabolism. In contrast hereto, the compounds of the pre-sent invention increases the metabolism, and they are therefore believed to be particular suited for maintaining a weight loss.

The compounds of the present invention are also believed to be particular well-suited for the treatment of diseases or disorders where reactive oxygen species are involved in the etiology, and wherein a reduction in the amount of reactive oxygen species are beneficial. In one embodiment, the invention thus provides a method of treating, and in particular preventing ageing and damages to the heart, endothelial cells and neuronal tissue, diabetic microvascular diseases in the retina, the renal glomerus and the peripheral nerve cells, the method comprising administering to a patient in need thereof a therapeutically effective amount of one or more compound of the present invention to a patient need thereof.

The subject may be any mammal suffering from a condition benefiting from increased mitochondrial respiration. Such mammals may include, for instance, horses, cows, sheep, pigs, mice, rats, dogs, cats, primates such as chimpanzees, gorillas, rhesus monkeys, and, most preferably, humans.

It is well-known that many compounds used to combat insects and parasites, i.e. insecticides and parasiticides, are chemical uncouplers. It is thus believed that uncouplers according to the present invention could be used as insecticides or parasiticides.

In the methods of the present invention, the compounds of the present invention may be administered alone or in combination with other therapeutically active compounds, either concomitantly or sequentially, and at any suitable ratios. Such further active compounds may be selected from antidiabetic agents, antihyperlipidemic agents, antiobesity agents, antihypertensive agents and agents for the treatment of complications resulting from or associated with diabetes.

Suitable antidiabetic agents include insulin, GLP-1 (glucagon like peptide-1) derivatives such as those disclosed in WO 98/08871 (Novo Nordisk A/S), which is incorporated herein by reference, as well as orally active hypoglycemic agents.

Suitable orally active hypoglycemic agents preferably include imidazolines, sulfonylureas, biguanides, meglitinides, oxadiazolidinediones, thiazolidinediones, insulin sensitizers, α-glucosidase inhibitors, agents acting on the ATP-dependent potassium channel of the pancreatic β-cells eg potassium channel openers such as those disclosed in WO 97/26265, WO 99/03861 and WO 00/37474 (Novo Nordisk A/S) which are incorporated herein by reference, potassium channel openers, such as ormitiglinide, potassium channel blockers such as nateglinide or BTS-67582, glucagon antagonists such as those disclosed in WO 99/01423 and WO 00/39088 (Novo Nordisk A/S and Agouron Pharmaceuticals, Inc.), all of which are incorporated herein by reference, GLP-1 agonists such as those disclosed in WO 00/42026 (Novo Nordisk A/S and Agouron Pharmaceuticals, Inc.), which are incorporated herein by reference, DPP-IV (dipeptidyl peptidase-IV) inhibitors, PTPase (protein tyrosine phosphatase) inhibitors, glucokinase activators, such as those described in WO 02/08209 to Hoffmann La Roche, inhibitors of hepatic enzymes involved in stimulation of gluconeogenesis and/or glycogenolysis, glucose uptake modulators, GSK-3 (glycogen synthase kinase-3) inhibitors, compounds modifying the lipid metabolism such as antihyperlipidemic agents and antilipidemic agents, compounds lowering food intake, and PPAR (peroxisome proliferator-activated receptor) and RXR (retinoid X receptor) agonists such as ALRT-268, LG-1268 or LG-1069.

In one embodiment of the methods, the compound of the present invention may be administered in combination with insulin or insulin analogues.

In one embodiment, the compound of the present invention may be administered in combination with a sulphonylurea eg tolbutamide, chlorpropamide, tolazamide, glibenclamide, glipizide, glimepiride, glicazide or glyburide.

In one embodiment, the compound of the present invention may be administered in combination with a biguanide eg metformin.

In one embodiment of the methods of the present invention, the compound of the present invention may be administered in combination with a meglitinide eg repaglinide or senaglinide/nateglinide.

In one embodiment, the compound of the present invention may be administered in combination with a thiazolidinedione insulin sensitizer, e.g. troglitazone, ciglitazone, pioglitazone, rosiglitazone, isaglitazone, darglitazone, englitazone, CS-011/CI-1037 or T 174 or the compounds disclosed in WO 97/41097 (e.g. 5-[[4-[3-methyl-4-oxo-3,4-dihydro-2-quinazolinyl]methoxy]phenylmethyl]thiazolidine-2,4-dione), WO 97/41119, WO 97/41120, WO 00/41121 and WO 98/45292, which are incorporated herein by reference.

In one embodiment, the compound of the present may be administered in combination 039242, KRP-297, GW-409544, CRE-16336, AR-H049020, LY510929, MBX-102, CLX-0940, GW-501516 or the compounds disclosed in WO 99/19313 (NN622/DRF-2725), WO 00/50414, WO 00/63191, WO 00/63192, WO 00/63193 and WO 00/23425, WO 00/23415, WO 00/23451, WO 00/23445, WO 00/23417, WO 00/23416, WO 00/63153, WO 00/63196, WO 00/63209, WO 00/63190 and WO 00/63189, which are incorporated herein by reference.

In one embodiment, the compound of the present invention may be administered in combination with an α-glucosidase inhibitor eg voglibose, emiglitate, miglitol or acarbose.

In one embodiment, the compound of the present invention may be administered in combination with a glycogen phosphorylase inhibitor eg the compounds described in WO 97/09040.

In one embodiment, the compound of the present may be administered in combination with a glucokinase activator.

In one embodiment, the compound of the present invention may be administered in combination with an agent acting on the ATP-dependent potassium channel of the pancreatic β-cells eg tolbutamide, glibenclamide, glipizide, glicazide, BTS-67582 or repaglinide.

In one embodiment, the compound of the present invention may be administered in combination with nateglinide.

In one embodiment, the compound of the present invention may be administered in combination with an antihyperlipidemic agent or a antilipidemic agent eg cholestyramine, colestipol, clofibrate, gemfibrozil, lovastatin, pravastatin, simvastatin, probucol or dextrothyroxine.

In one embodiment, the compound of the present may be administered in combination with more than one of the above-mentioned compounds e.g. in combination with metformin and a sulphonylurea such as glyburide; a sulphonylurea and acarbose; nateglinide and metformin; acarbose and metformin; a sulfonylurea, metformin and troglitazone; insulin and a sulfonylurea; insulin and metformin; insulin, metformin and a sulfonylurea; insulin and troglitazone; insulin and lovastatin; etc.

In one embodiment, the compound of the present invention may be administered in combination with one or more antiobesity agents or appetite regulating agents.

Such agents may be selected from the group consisting of CART (cocaine amphetamine regulated transcript) agonists, NPY (neuropeptide Y) antagonists, MC3 (melanocortin 3) agonists, MC4 (melanocortin 4) agonists, orexin antagonists, TNF (tumor necrosis factor) agonists, CRF (corticotropin releasing factor) agonists, CRF BP (corticotropin releasing factor binding protein) antagonists, urocortin agonists, β3 adrenergic agonists such as CL-316243, AJ-9677, GW-0604, LY362884, LY377267 or AZ-40140, MSH (melanocyte-stimulating hormone) agonists, MCH (melanocyte-concentrating hormone) antagonists, CCK (cholecystokinin) agonists, serotonin reuptake inhibitors (fluoxetine, seroxat or citalopram), norepinephrine reuptake inhibitors (e.g. sibutramine), 5HT (serotonin) agonists, bombesin agonists, galanin antagonists, growth hormone, growth factors such as prolactin or placental lactogen, growth hormone releasing compounds, TRH (thyreotropin releasing hormone) agonists, UCP 2 or 3 (uncoupling protein 2 or 3) modulators, leptin agonists, DA (dopamine) agonists (bromocriptin, doprexin), lipase/amylase inhibitors, PPAR modulators, RXR modulators, TR β agonists, adrenergic CNS stimulating agents, AGRP (agouti related protein) inhibitors, H3 histamine antagonists such as those disclosed in WO 00/42023, WO 00/63208 and WO 00/64884, which are incorporated herein by reference, exendin-4, GLP-1 agonists and ciliary neurotrophic factor. Further antiobesity agents are bupropion (antidepressant), topiramate (anticonvulsant), ecopipam (dopamine D1/D5 antagonist), naltrexone (opioid antagonist), and peptide $YY_{3-36}$ (Batterham et al, Nature 418, 650-654 (2002)).

In one embodiment, the antiobesity agent is leptin.

In one embodiment, the antiobesity agent is a lipase inhibitor eg orlistat.

In one embodiment, the antiobesity agent is an adrenergic CNS stimulating agent eg dexamphetamine, amphetamine, phentermine, mazindol phendimetrazine, diethylpropion, fenfluramine or dexfenfluramine.

In a further embodiment, the compounds of the present invention may be administered in combination with one or more antihypertensive agents. Examples of antihypertensive agents are β-blockers such as alprenolol, atenolol, timolol, pindolol, propranolol and metoprolol; ACE (angiotensin converting enzyme) inhibitors such as benazepril, captopril, enalapril, fosinopril, lisinopril, quinapril and ramipril; calcium channel blockers such as nifedipine, felodipine, nicardipine, isradipine, nimodipine, diltiazem and verapamil; and α-blockers such as doxazosin, urapidil, prazosin and terazosin.

It should be understood that any suitable combination of the compounds according to the invention with diet and/or exercise, one or more of the above-mentioned compounds and optionally one or more other active substances are considered to be within the scope of the present invention.

The present invention also provides pharmaceutical compositions comprising as an active ingredient, at least one compound of the present invention, preferably in a therapeutically effective amount, suitable for any of the methods according to the present invention together with one or more pharmaceutically acceptable carriers or excipients. Said pharmaceutical compositions may also comprise any of the further active compounds as indicated above The pharmaceutical composition is preferably in unit dosage form, comprising from about 0.05 mg to about 1000 mg, preferably from about 0.1 mg to about 500 mg and especially preferred from about 0.5 mg to about 200 mg of a compound suitable for any of the methods described above.

Pharmaceutical Compositions

The compounds of the present invention may be administered alone or in combination with pharmaceutically acceptable carriers or excipients, in either single or multiple doses. The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, 20$^{th}$ Edition, Gennaro, Ed., Mack Publishing Co., Easton, Pa., 2000.

The pharmaceutical compositions may be specifically formulated for administration by any suitable route such as the oral, rectal, nasal, pulmonary, topical (including buccal and sublingual), transdermal, intracisternal, intraperitoneal, vaginal and parenteral (including subcutaneous, intramuscular, intrathecal, intravenous and intradermal) route, the oral route being preferred. It will be appreciated that the preferred route will depend on the general condition and age of the subject to be treated, the nature of the condition to be treated and the active ingredient chosen.

Pharmaceutical compositions for oral administration include solid dosage forms such as hard or soft capsules, tablets, troches, dragees, pills, lozenges, powders and granules. Where appropriate, they can be prepared with coatings such as enteric coatings or they can be formulated so as to provide controlled release of the active ingredient such as sustained or prolonged release according to methods well known in the art.

Liquid dosage forms for oral administration include solutions, emulsions, aqueous or oily suspensions, syrups and elixirs.

Pharmaceutical compositions for parenteral administration include sterile aqueous and non-aqueous injectable solutions, dispersions, suspensions or emulsions as well as sterile powders to be reconstituted in sterile injectable solutions or dispersions prior to use. Depot injectable formulations are also contemplated as being within the scope of the present invention.

Other suitable administration forms include suppositories, sprays, ointments, cremes, gels, inhalants, dermal patches, implants etc.

A typical oral dosage is in the range of from about 0.001 to about 100 mg/kg body weight per day, preferably from about 0.01 to about 50 mg/kg body weight per day, and more preferred from about 0.05 to about 10 mg/kg body weight per day administered in one or more dosages such as 1 to 3 dosages. The exact dosage will depend upon the frequency and mode of administration, the sex, age, weight and general condition of the subject treated, the nature and severity of the condition treated and any concomitant diseases to be treated and other factors evident to those skilled in the art.

The formulations may conveniently be presented in unit dosage form by methods known to those skilled in the art. A typical unit dosage form for oral administration one or more times per day such as 1 to 3 times per day may contain from 0.05 to about 1000 mg, preferably from about 0.1 to about 500 mg, and more preferred from about 0.5 mg to about 200 mg.

For parenteral routes such as intravenous, intrathecal, intramuscular and similar administration, typically doses are in the order of about half the dose employed for oral administration.

The compounds for use according to the present invention are generally utilized as the free substance or as a pharmaceutically acceptable salt thereof. Examples are an acid addition salt of a compound having the utility of a free base and a base addition salt of a compound having the utility of a free acid. The term "pharmaceutically acceptable salts" refers to non-toxic salts of the compounds for use according to the present invention which salts are generally prepared by reacting the free base with a suitable organic or inorganic acid or by reacting the acid with a suitable organic or inorganic base. When a compound for use according to the present invention contains a free base such salts are prepared in a conventional manner by treating a solution or suspension of the compound with a chemical equivalent of a pharmaceutically acceptable acid. When a compound for use according to the present invention, contains a free acid such salts are prepared in a conventional manner by treating a solution or suspension of the compound with a chemical equivalent of a pharmaceutically acceptable base. Physiologically acceptable salts of a compound with a hydroxy group include the anion of said compound in combination with a suitable cation such as sodium or ammonium ion. Other salts which are not pharmaceutically acceptable may be useful in the preparation of compounds of the invention and these form a further aspect of the invention.

For parenteral administration, solutions of the compounds for use according to the pre-sent invention in sterile aqueous solution, aqueous propylene glycol or sesame or peanut oil may be employed. Such aqueous solutions should be suitably buffered if necessary and the liquid diluent first rendered isotonic with sufficient saline or glucose. The aqueous solutions are particularly suitable for intravenous, intramuscular, subcutaneous and intraperitoneal administration. The sterile aqueous media employed are all readily available by standard techniques known to those skilled in the art.

Suitable pharmaceutical carriers include inert solid diluents or fillers, sterile aqueous solution and various organic solvents. Examples of solid carriers are lactose, terra alba, sucrose, cyclodextrin, talc, gelatine, agar, pectin, acacia, magnesium stearate, stearic acid and lower alkyl ethers of cellulose. Examples of liquid carriers are syrup, peanut oil, olive oil, phospholipids, fatty acids, fatty acid amines, polyoxyethylene and water. Similarly, the carrier or diluent may include any sustained release material known in the art, such as glyceryl monostearate or glyceryl distearate, alone or mixed with a wax. The pharmaceutical compositions formed by combining the compounds for use according to the present invention and the pharmaceutically acceptable carriers are then readily administered in a variety of dosage forms suitable for the disclosed routes of administration. The formulations may conveniently be presented in unit dosage form by methods known in the art of pharmacy.

Formulations of the present invention suitable for oral administration may be presented as discrete units such as capsules or tablets, each containing a predetermined amount of the active ingredient, and which may include a suitable excipient. Furthermore, the orally available formulations may be in the form of a powder or granules, a solution or suspension in an aqueous or non-aqueous liquid, or an oil-in-water or water-in-oil liquid emulsion.

Compositions intended for oral use may be prepared according to any known method, and such compositions may contain one or more agents selected from the group consisting of sweetening agents, flavouring agents, colouring agents, and preserving agents in order to provide pharmaceutically elegant and palatable preparations. Tablets may contain the active ingredient in admixture with non-toxic pharmaceutically-acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch or alginic acid; binding agents, for example, starch, gelatine or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,356,108; 4,166,452; and 4,265,874, incorporated herein by reference, to form osmotic therapeutic tablets for controlled release.

Formulations for oral use may also be presented as hard gelatine capsules where the active ingredient is mixed with an inert solid diluent, for example, calcium carbonate, calcium phosphate or kaolin, or a soft gelatine capsules wherein the active ingredient is mixed with water or an oil medium, for example peanut oil, liquid paraffin, or olive oil.

Aqueous suspensions may contain the compound for use according to the present invention in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide such as lecithin, or condensation products of an alkylene oxide with fatty acids, for example polyoxyethylene stearate, or condensation products of ethylene oxide with long chain aliphatic alcohols, for example, heptadecaethyl-eneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more colouring agents, one or more flavouring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as a liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water provide the active compound in admixture with a dispersing or wetting agent, suspending agent and one or more preservatives. Suitable dispersing or wetting agents and suspending agents are exemplified by those already mentioned above. Additional excipients, for example, sweetening, flavouring, and colouring agents may also be present.

The pharmaceutical compositions comprising compounds for use according to the present invention may also be in the form of oil-in-water emulsions. The oily phase may be a vegetable oil, for example, olive oil or arachis oil, or a mineral oil, for example a liquid paraffin, or a mixture thereof. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavouring and colouring agents. The pharmaceutical compositions may be in the form of a sterile injectable aqueous or oleaginous suspension. This suspension may be formulated according to the known methods using suitable dispersing or wetting agents and suspending agents described above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution, and isotonic sodium chloride solution. In addition, sterile, fixed oils are conveniently employed as solvent or suspending medium. For this purpose, any bland fixed oil may be employed using synthetic mono- or diglycerides. In addition, fatty acids such as oleic acid find use in the preparation of injectables.

The compositions may also be in the form of suppositories for rectal administration of the compounds of the invention. These compositions can be prepared by mixing the drug with a suitable non-irritating excipient which is solid at ordinary temperatures but liquid at the rectal temperature and will thus melt in the rectum to release the drug. Such materials include cocoa butter and polyethylene glycols, for example.

For topical use, creams, ointments, jellies, solutions of suspensions, etc., containing the compounds of the invention are contemplated. For the purpose of this application, topical applications shall include mouth washes and gargles.

The compounds of the present invention may also be administered in the form of liposome delivery systems, such as small unilamellar vesicles, large unilamellar vesicles, and multilamellar vesicles. Liposomes may be formed from a variety of phospholipids, such as cholesterol, stearylamine, or phosphatidylcholines.

In addition, some of the compounds of the present invention may form solvates with water or common organic solvents. Such solvates are also encompassed within the scope of the invention.

Thus, in a further embodiment, there is provided a pharmaceutical composition comprising a compound for use according to the present invention, or a pharmaceutically acceptable salt, solvate, or prodrug thereof, and one or more pharmaceutically acceptable carriers, excipients, or diluents.

If a solid carrier is used for oral administration, the preparation may be tabletted, placed in a hard gelatine capsule in powder or pellet form or it can be in the form of a troche or lozenge. The amount of solid carrier will vary widely but will usually be from about 25 mg to about 1 g. If a liquid carrier is used, the preparation may be in the form of a syrup, emulsion, soft gelatine capsule or sterile injectable liquid such as an aqueous or non-aqueous liquid suspension or solution.

A typical tablet that may be prepared by conventional tabletting techniques may contain:

| Core: | |
|---|---|
| Active compound (as free compound or salt thereof) | 5.0 mg |
| Lactosum Ph. Eur. | 67.8 mg |
| Cellulose, microcryst. (Avicel) | 31.4 mg |
| Amberlite ® IRP88* | 1.0 mg |
| Magnesii stearas Ph. Eur. | q.s. |
| Coating: | |
| Hydroxypropyl methylcellulose | approx. 9 mg |
| Mywacett 9-40 T** | approx. 0.9 mg |

*Polacrillin potassium NF, tablet disintegrant, Rohm and Haas.
**Acylated monoglyceride used as plasticizer for film coating.

If desired, the pharmaceutical composition comprising a compound for use according to the present invention may comprise a compound for use according to the present invention in combination with further active substances such as those described in the foregoing.

The present invention also provides methods for the preparation of compounds for use according to the present invention. The compounds can be prepared readily according to the following general procedures (in which all variables are as defined before, unless so specified) using readily available starting materials, reagents and conventional synthesis procedures. In these reactions, it is also possible to make use of variants which are themselves known to those of ordinary skill in this art, but are not mentioned in greater detail.

EXAMPLES

HPLC-MS (Method A)

The following instrumentation is used:
Hewlett Packard series 1100 G1312A Bin Pump
Hewlett Packard series 1100 Column compartment
Hewlett Packard series 1100 G1315A DAD diode array detector
Hewlett Packard series 1100 MSD
Sedere 75 Evaporative Light Scattering detector
The instrument is controlled by HP Chemstation software.
The HPLC pump is connected to two eluent reservoirs containing:
A: 0.01% TFA in water
B: 0.01% TFA in acetonitrile
The analysis is performed at 40° C. by injecting an appropriate volume of the sample (preferably 1 µl) onto the column which is eluted with a gradient of acetonitrile.

The HPLC conditions, detector settings and mass spectrometer settings used are giving in the following table.
Column: Waters Xterra MS C-18×3 mm id 5 µm
Gradient: 5%-100% acetonitrile linear during 7.5 min at 1.5 ml/min
Detection: 210 nm (analogue output from DAD (diode array detector))
ELS (analogue output from ELS)
MS ionisation mode API-ES
Scan 100-1000 amu step 0.1 amu
After the DAD the flow is divided yielding approx 1 ml/min to the ELS and 0.5 ml/min to the MS.

General procedure (A)

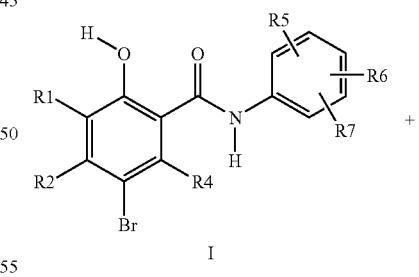

I

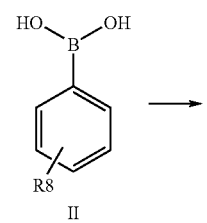

II

-continued

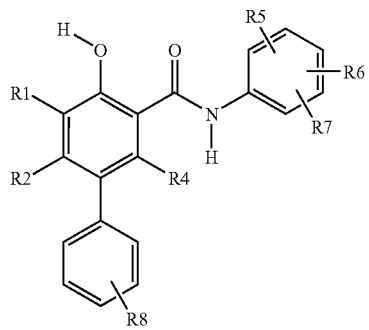

III

To a solution of the bromo-substituted salicylanilide I (1 equivalent) in dioxane the appropriate substituted aryl boronic acid was added. The appropriate palladium catalyst was added together with the appropriate base, and the reaction mixture was heated at reflux for 5-20 hours. The reaction mixture was evaporated. Water was added to the residue, and the water phase was extracted with an organic solvent like ethylacetate, diethylether, dichloromethane. The organic phase was dried over sodium sulphate and evaporated.

Step A: Aquae's work up followed by crystallisation

Step B: Aquae's work up followed by column chromatography

General procedure (B)

-continued

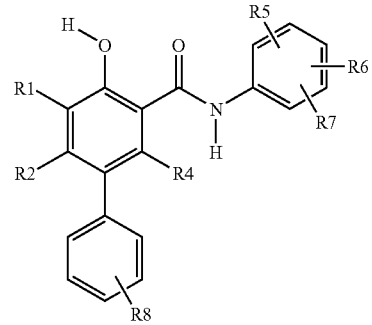

III

To a solution of the bromo-substituted salicylanilide I (1 equivalent) in acetonitrile the appropriate substituted aryl tin compound was added. The appropriate palladium catalyst was added together with the appropriate base, and the reaction mixture was heated at reflux for 5-20 hours. The reaction mixture was evaporated. Water was added to the residue, and the water phase was extracted with an organic solvent like ethylacetate, diethylether, dichloromethane. The organic phase was dried over sodium sulphate and evaporated.

Step A: Aquae's work up followed by crystallisation

Step B: Aquae's work up followed by column chromatography

General procedure (C)

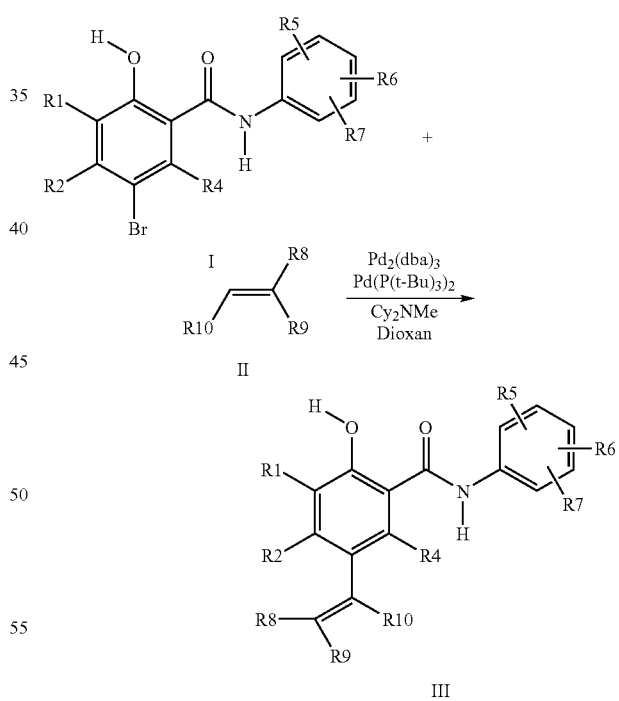

To a solution of the bromo compound A (1 equivalent) in an organic solvent like dioxane or tetrahydrofuran, $Pd_2(dba)_3$ (0.01 equivalent) and $Pd(P(t-bu)_3)_2$ (0.02 equivalent) was added. To this solution the appropriate vinyl compound B (1 equivalent) followed by dicyclohexylmethylamine (1.1 equivalent) was added. The reaction mixture was stirred at room temperature for 1-3 days. The compounds were isolated by aqua's work-up followed by column chromatography.

General procedure (D)

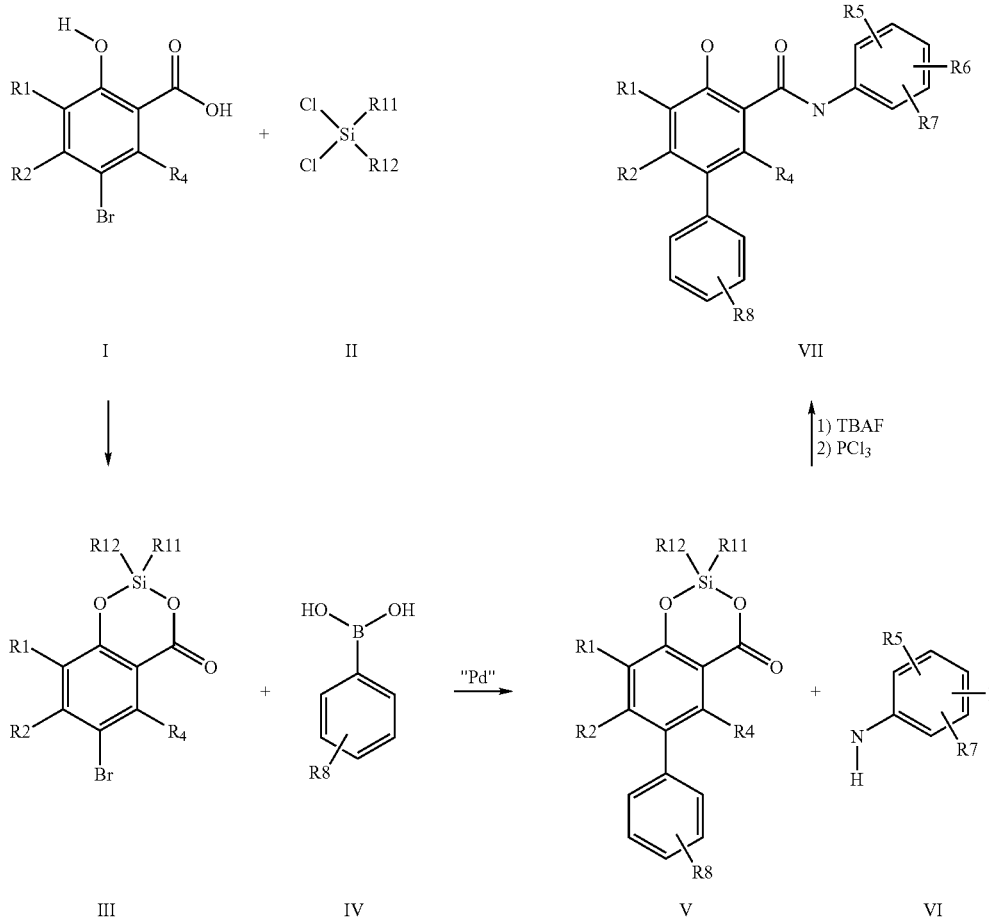

The substituted salicylic acid I is protected with di-alkyl-dichloro-silane II after reflux in toluene to form a compound of formula III. The bromo derivative III is reacted with a boronic acid of formula IV under palladium catalysed cross coupling reaction conditions to give compounds of formula V.

Compounds of formula V is hydrolysed to the free salicylic acid with aqua's base or tetrabutylammonium fluoride (TBAF). The free acid is reacted with an aniline Vi under standard conditions to give compounds of formula VII.

General procedure (E)

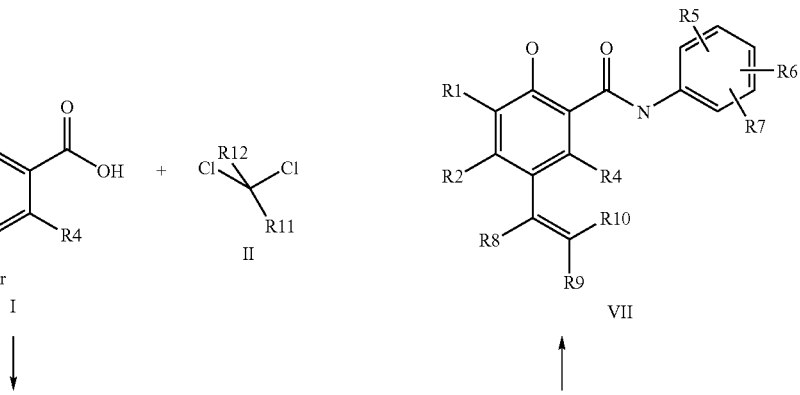

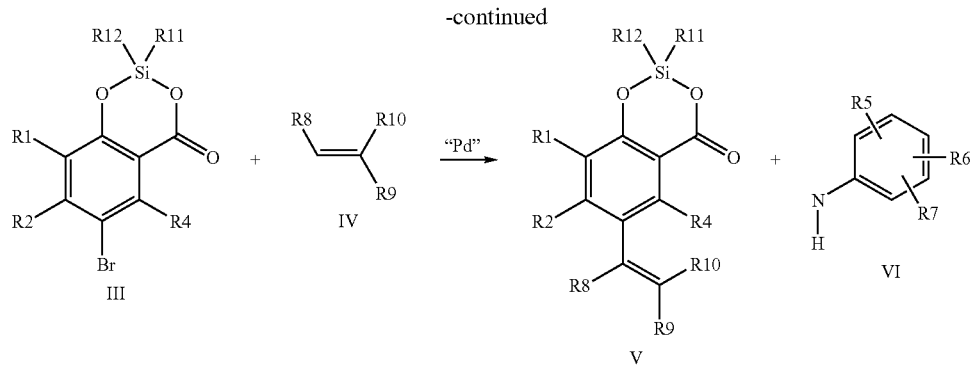

The substituted salicylic acid I is protected with di-alkyl-dichloro silane II after reflux in toluene to form a compound of formula III. The bromo derivative III is reacted with an appropriate alkene or alkyne compound of formula IV under palladium catalysed cross coupling reaction conditions to give compounds of formula V. Compounds of formula V is hydrolysed to the free salicylic acid with aqua's base or tetrabutylammonium fluoride (TBAF). The free acid is reacted with an aniline VI under standard conditions to give compounds of formula VII.

Example 1

General Procedure (A)

5-tert-Butyl-4-hydroxy-2-methyl-biphenyl-3-carboxylic acid (2-chloro-4-nitro-phenyl)amide

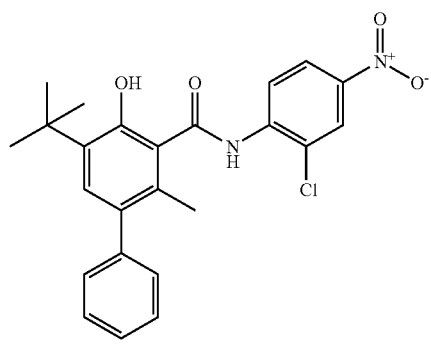

Step B: To a solution of 3-Bromo-5-tert-butyl-N-(2-chloro-4-nitro-phenyl)-6-hydroxy-2-methyl-benzamide (0.18 g, 0.4 mmole) in dioxane (5 ml) under nitrogen phenylboronic acid (50.0 mg, 0.4 mmole), tetrakis(triphenylphosphine)palladium(0) (10 mg, 0.009 mmole) and sodium carbonate (1.41 ml, 2 M solution in water) were added. The reaction mixture was heated at 100° C. for 6 hours. The reaction mixture was evaporated, diluted with ethyl acetate and the organic phase was washed with citric acid solution (10%). The organic phase was dried over sodium sulphate and evaporated. The crude compound was purified by column chromatography.

$^1$H (400 MHz, CHLOROFORM-D): δ ppm 1.42 (s, 9H) 7.31 (s, 1H) 2.45 (s, 3H) 7.25-7.35 (m, 4H) 7.40-7.50 (m, 2H) 8.25 (dd, 1H) 8.32 (d, 1H) 8.50 (s, 1H) 8.90 (d, 1H) 9.60 (s, 1H); HPLC-MS (Method A): m/z=439, 441 (M+1); $R_t$=5.99.

Example 2

General Procedure (B)

(E) 3-tert-Butyl-N-(2-chloro-4-cyano-phenyl)-2-hydroxy-5-styryl-benzamide

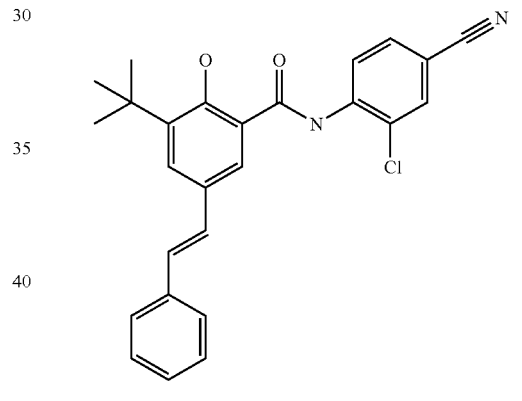

Step B: To a solution of 3-Bromo-5-tert-butyl-N-(2-chloro-4-nitro-phenyl)-6-hydroxy (0.2 g, 0.5 mmole) in acetonitrile (5 ml) phenylethenyltin (0.25 g, 0.63 mmole) and bis(triphenylphosphine)palladium(II) chloride (Acros organics, 35.0 mg, 0.05 mmol), were added under a nitrogen atmosphere. The mixture was submitted to microwaves (Emry's Optimizer EXP, single mode instrument from Personal Chemistry, 130° C., 300 sek). The reaction was evaporated, dissolved in water and dichloromethane, and then acidified with trifluoroacetic acid. The organic layer was evaporated and the crude compound was purified by column chromatography.

$^1$H (400 MHz, CHLOROFORM-D): δ ppm 1.49 (s, 9H) 6.99 (d, 1H) 7.08 (d, 1H) 7.47 (s, 1H) 7.50-7.55 (m, 5H), 7.60 (s, 1H) 7.64-7.68 (m, 1H) 7.73 (s, 1H) 8.67 (d, J=8.59 Hz, 1H) 8.77 (s, 1H) 12.21 (s, 1H) HPLC-MS (Method A): m/z=409 (M+1); $R_t$=5.65.

Example 3

General Procedure (A)

5-tert-Butyl-4-hydroxy-2-methyl-biphenyl-3-carboxylic acid (4-cyano-2-trifluoromethoxy-phenyl)-amide

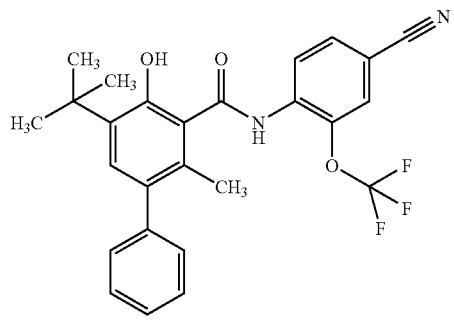

Step B: To a solution of 3-Bromo-5-tert-butyl-N-(2-trifluoromethoxy-4-cyano-phenyl)-6-hydroxy-2-methyl-benzamide (0.141 g, 0.3 mmole) in dioxane (5 ml) under nitrogen, phenylboronic acid (37.0 mg, 0.3 mmole), tetrakis(triphenylphosphine)palladium(0) (7 mg, 0.006 mmole) and sodiumcarbonate (1.05 ml, 2 M solution in water) were added. The reaction mixture was heated at 100° C. for 48 hours. The reaction mixture was evaporated, diluted with ethyl acetate and the organic phase was washed with citric acid solution (10%). The organic phase was dried over sodium sulphate and evaporated. The crude compound was purified by column chromatography.

$^1$H (400 MHz, CHLOROFORM-D): δ ppm 1.43 (s, 9H) 2.39 (s, 3H) 7.27-7.41 (m, 5H) 7.45 (dd, 1H), 7.48 (s, 1H) 7.61 (s, 1H) 7.68 (d, J=8.59 Hz, 1H) 8.21 (s, 1H) 8.87 (d, J=8.59 Hz, 1H) 9.77 (s, 1H); HPLC-MS (Method A): m/z=469 (M+1); $R_f$=5.65.

Example 4

General Procedure (A)

5-tert-Butyl-4'-cyano-4-hydroxy-2-methyl-biphenyl-3-carboxylic acid (4-cyano-2-trifluoromethoxy-phenyl)-amide

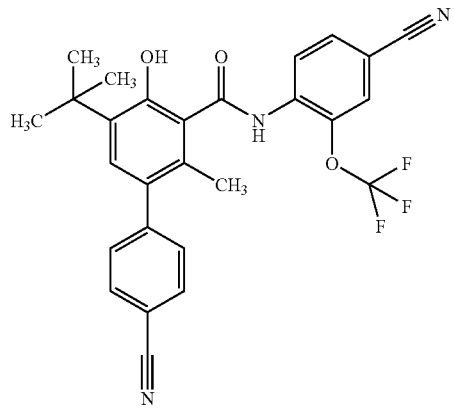

Step B: To a solution of 3-bromo-5-tert-butyl-N-(2-trifluoromethoxy-4-cyano-phenyl)-6-hydroxy-2-methyl-benzamide (0.141 g, 0.3 mmole) in dioxane (5 ml) under nitrogen, 4-cyanophenylboronic acid (44.0 mg, 0.3 mmole), tetrakis (triphenylphosphine)palladium(0) (7 mg, 0.006 mmole) and sodiumcarbonate (1.05 ml, 2 M solution in water) were added. The reaction mixture was heated at 100° C. for 6 hours. The reaction mixture was evaporated, diluted with ethyl acetate and the organic phase was washed with citric acid solution (10%). The organic phase was dried over sodium sulphate and evaporated. The crude compound was purified by column chromatography.

$^1$H (400 MHz, CHLOROFORM-D): δ ppm 1.43 (s, 9H) 2.37 (s, 3H) 7.24 (s, 1H) 7.41 (d, J=8.08 Hz, 2H) 7.62 (s, 1H) 7.66-7.72 (m, 1H) 7.74 (d, J=8.08 Hz, 2H) 8.16 (s, 1H) 8.85 (d, J=8.59 Hz, 1H) 9.75 (s, 1H); HPLC-MS (Method A): m/z=494 (M+1); $R_f$=5.27.

Example 5

General Procedure (A)

3-tert-Butyl-N-(2-chloro-4-cyano-phenyl)-5-(5-cyano-thiophen-2-yl)-2-hydroxy-benzamide

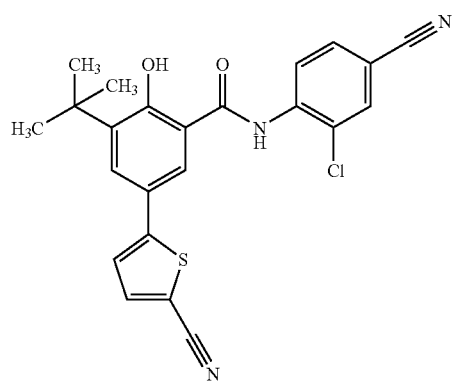

Step B: To a solution of 3-bromo-5-tert-butyl-N-(2-chloro-4-cyano-phenyl)-6-hydroxy-benzamide (0.141 g, 0.34 mmole) in dimethoxyethane (15 ml) under nitrogen, 4-cyanophenylboronic acid (44.0 mg, 0.3 mmole), tetrakis(triphenylphosphine)palladium(0) (63 mg, 0.055 mmole) and sodium hydrogen carbonate (5.5 ml, saturated solution in water) were added. The reaction mixture was heated at 80° C. for 23 hours. The reaction mixture was evaporated, diluted with ethyl acetate and the organic phase was washed with citric acid solution (10%). The organic phase was dried over sodium sulphate and evaporated. The crude compound was purified by column chromatography.

$^1$H (400 MHz, CHLOROFORM-D): δ ppm 1.50 (s, 9H) 7.20 (d, J=4.04 Hz, 1H) 7.61 (m, 2H) 7.67 (dd, J=8.59, 2.02 Hz, 1H) 7.70 (d, J=2.02 Hz, 1H) 7.78 (s, 1H) 8.65 (d, J=8.59 Hz, 1H) 8.74 (s, 1H) 12.35 (s, 1H); HPLC-MS (Method A): m/z=436, 438 (M+1); $R_f$=5.65.

Example 6

General Procedure (A)

5-Benzo[b]thiophen-2-yl-3-tert-butyl-N-(2-chloro-4-cyano-phenyl)-2-hydroxy-benzamide

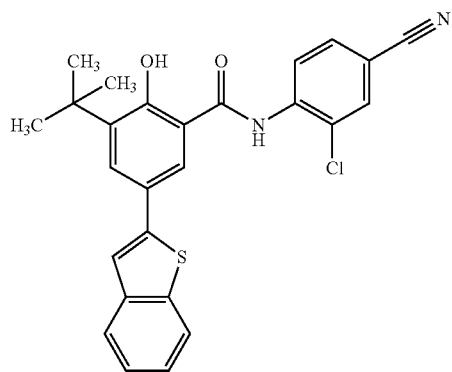

Step B: The title compound was prepared from 3-bromo-5-tert-butyl-N-(2-chloro-4-cyanophenyl)-6-hydroxy-benzamide and benzothiophen-2-boronic acid HPLC-MS (Method A): m/z=462 (M+1); $R_t$=6.05.

By the procedures described above the following compounds can be prepared

Pharmacological Methods

Assay (I): Glucose Utilisation in a Human Epithelia Cell Line (FSK-4 Cells)

Assay Description:

The assay measures indirectly the activity of the respiratory chain in FSK-4 cells by using D-(6-$^3$H(N))-glucose. The $^3$H-proton will first be released in the TCA cyclus and transported to the respiratory chain where it will be incorporated into water. The water is thereafter separated from the D-(6-$^3$H(N))-glucose by evaporation. Finally, the radioactivity in the water is determined using a Topcounter.

Method:

FSK-4 cells obtained from ATCC (Maryland, USA), are cultured in growth medium (McCoy's medium with the following addition 100 units/ml penicillin and streptomycin and 10% FCS (fetal calf serum)) at 37° C. and 5% $CO_2$. All media are obtained by Gibco (Life Technologies, Maryland, USA) where not otherwise mentioned.

At day zero the cells are harvested using trypsin-EDTA and washed in assay medium (MEM medium with the following addition 1× non-essential amino acids (M7145, 2 mM glutamin, 100 units/ml pencillin and streptomycin, 0.0075% sodium bicarbonate, 1 mM sodium pyrovate and 2% horse serum) using centrifugation. The cells are plated into single StripPlates wells (Corning B.V. Life Sciences, The Netherlands) that are placed into 24-well plates (Corning B.V. Life Sciences, The Netherlands) with a concentration of 1.5×10$^4$ cells/100 μl assay medium/well. The cells are then incubated at 37° C. and 5% $CO_2$ overnight.

The next day the compounds to be tested are diluted to different concentrations in DMSO (Sigma, Missouri, USA) to 100 times final concentration. They are then diluted to a final concentration in assay medium containing 10 μCi/ml D-(6-$^3$H(N))-glucose (PerkinElmer Life Sciences Inc., Boston, USA). The medium is removed from the cells and 200 μl of the compound dilutions are added in duplicates. The cells are then incubated for another 24 hours at 37° C. and 5% $CO_2$. Finally the cells are lysed by adding 50 μl 10% TCA (trichloroacetate). 300 μl of sterile water is then added to the 24-wells that surrounds the Strip-Plate wells. The plate is sealed with Top-seal-tape (Packard, PerkinElmer Life Sciences Inc., Boston, USA) and the plate is incubated in a heating cupboard at 50° C. to equilibrium the radioactive water formed in the respiratory chain into the water in the 24-well plate by evaporate. The plates incubate for 8 hours where the heating cupboard is turned off. The top seal is removed when the samples have reached room temperature. One ml scintillation liquid (Packard Microscient, PerkinElmer Life Sciences Inc., Boston, USA) is added to all the samples and the radioactivity is determined using a Topcounter (Packard, PerkinElmer Life Sciences Inc., Boston, USA). Non-specific activity is determined by evaporating 200 μl of the dilution medium containing the D-(6-$^3$H(N))-glucose into 300 μl sterile water, and total radioactivity is determined by counting 5 μl assay medium with 10 μCi/ml D-(6-$^3$H(N))-glucose.

Calculations

The half maximal concentration ($EC_{50}$) and maximal efficacy ($E_{max}$) are calculated using the Hill equation in GraphPad Prism 3.0 (GraphPad software, Inc.). In studies where the linear slope is determined the following concentration of the compound is used; 5×, 3×, 2×, 1.5×, 1.25×, 1×, 0.85×, 0.7×, 0.5×, 0.3×, 0.2× and 0×$EC_{50}$. From the percentage increase in glucose utilisation the linear slope is calculated using the Michaelis-Menten equation.

Assay (II): The Effect of Chemical Uncouplers on Mitochondrial Respiration Using Isolated Mitochondria.

This assay is used to investigate if the increase in glucose utilisation caused by the test compounds observed in the glucose utilisation assay is due to an increase in the respiration of the mitochondria. This is done by measuring oxygen consumption in isolated rat liver mitochondria.

A Clark oxygen electrode is used to determine the oxygen consumption. The isolated mitochondria are added to assay medium (D-Mannitol 220 mM, MagnesiumCloride 5 mM, HEPES 2 mM and PotassiumPhosphate 5 mM, pH=7.4) containing rotenone (an inhibitor of complex 1) and oligomyocin (an inhibitor of the ATP-synthase) and the rate of oxygen consumptions is measured, when stabilized nutrient (e.g. succinate) is added and an increase in the rate of oxygen consumption is measured. When the rate of oxygen consumption again has stabilized the test compound is added and the oxygen consumption is measured. If the test compound stimulates the rate of oxygen consumption, it is regarded as a chemical uncoupler.

Assay (III): Identification of Chemical Uncouplers that Increase Energy Expenditure In Vivo The effect of the chemical uncouplers on energy expenditure (oxygen consumption) in vivo is determined by indirect calorimetry. Briefly, animals are placed in airtight chambers. Air is continuously led to and from the chambers. The gas concentrations of oxygen ($O_2$) and carbon dioxide ($CO_2$) in the air led to and from the chambers (inlet and outlet air) are recorded and the consumption of $O_2$ and the production of $CO_2$ are calculated. Based on the amount of $O_2$ consumed and $CO_2$ produced, energy expenditure is calculated. Compounds which at a given dose increase whole body energy expenditure without obvious deleterious effects are deemed to be chemical uncouplers that increase energy expenditure.

The invention claimed is:
1. A compound according to formula I

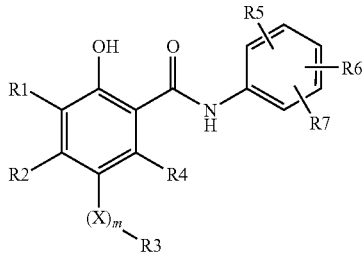

wherein X represent

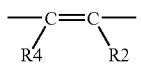

or —C≡C—, and m is 0, 1 or 2;
R1 represents branched $C_{1-6}$alkyl or phenyl;
R2 and R4 independently represent, hydrogen, $C_{1-6}$alkyl, $C_{1-6}$alkenyl, $C_{1-6}$alkynyl or $C_{1-6}$alkoxy;
R5, R6 and R7 together constitute a substitution pattern selected from the group consisting of 2-chloro-4-nitro; 2-chloro-4-cyano; 2-trifluoromethoxy-4-nitro; 2-trifluoromethoxy-4-cyano; 2-trifluoromethyl-4-(1-imidazolyl); and 2-methyl-4-(1-imidazolyl);
R3 represents $C_{1-6}$alkyl, $C_{1-6}$alkenyl, $C_{1-6}$alkynyl, $C_{1-6}$haloalkyl, aryl$C_{1-6}$alkyl, aryl$C_{1-6}$alkenyl, aryl$C_{1-6}$alkynyl, heteroaryl$C_{1-6}$alkyl, heteroaryl$C_{1-6}$alkenyl, heteroaryl$C_{1-6}$alkynyl, $C_{3-8}$cycloalkyl, aryl, or heteroaryl; wherein R3 may optionally be substituted with up to four substituents, R10, R11, R12, and R13, wherein R10, R11, R12, and R13 independently represent $C_{1-6}$alkyl, $C_{1-6}$alkylaryl, halogen, $C_{1-6}$haloalkyl, $C_{1-6}$hydroxyalkyl, $C_{1-6}$alkoxy, oxo, cyano, nitro, —(CH2)$_r$O R14, —SH, —S (O)$_p$ R15, —S(O)$_p$N(R14)(R15), —C(O)O R14, —OC(O)R14, —C(O)N(R14), —C(O)N(R14)(R15), —(CH2)$_r$N(R14)C(O)R15—, —B(OR14)(OR15), —(CH2)$_r$N(R14)(R15), or phenyl, wherein said phenyl is optionally substituted with one or more substituents selected from the group consisting of $C_{1-6}$alkyl, halogen, $C_{1-6}$haloalkyl, $C_{1-6}$hydroxyalkyl, cyano, nitro, —OR16—, —S(O)$_s$R16, —C(O)OR16, —OC(O)R16, —C(O)R16, —C(O)N(R16)(R17), —N(R16)(R17),(CH$_2$)$_s$N(R16)C(O)R17, —B(OR16)(OR17)—, —(CH2)$_r$OR16, or —(CH$_2$)$_r$N(16)(R17),
each R14 independently represents hydrogen, $C_{1-6}$haloalkyl, $C_{1-6}$hydroxyalkyl, $C_{1-6}$alkyl, $C_{1-6}$alkenyl, $C_{1-6}$alkynyl, $C_{3-8}$cycloalkyl, or phenyl optionally substituted with one or more substituents selected from the group consisting of $C_{1-6}$alkyl, halogen, $C_{1-6}$haloalkyl, $C_{1-6}$hydroxyalkyl and cyano;
R15 represents $C_{1-6}$haloalkyl, $C_{1-6}$hydroxyalkyl, $C_{1-6}$alkyl, $C_{1-6}$alkenyl, $C_{1-6}$alkynyl, $C_{3-8}$cycloalkyl, or phenyl optionally substituted with one or more substituents selected from the group consisting of $C_{1-6}$alkyl, halogen, $C_{1-6}$haloalkyl, $C_{1-6}$hydroxyalkyl and cyano;
or wherein R14 and R15, when attached to a nitrogen atom, together with said nitrogen atom form a $C_{3-8}$cycloalkyl or heteroaryl ring, optionally substituted with one or more $C_{1-6}$alkyl substituents;
each R16 and R17 independently represents hydrogen, $C_{1-6}$haloalkyl, $C_{1-6}$hydroxyalkyl, $C_{1-6}$alkyl, $C_{1-6}$alkenyl, $C_{1-6}$alkynyl or $C_{3-8}$cycloalkyl; or R16 and R17, when attached to a nitrogen atom, together with said nitrogen atom form a cycloalkyl or heteroaryl ring, optionally substituted with one or more alkyl substituents;
p and s, independently of each other, are an integer of 0, 1, or 2;
r and t, independently of each other, are an integer of 0, 1, 2, or 3;
q is 0, 1, 2;
provided that the compound is not N-(2-chloro-4-nitrophenyl)-3-tert-butyl-6-methylsalicylanilide, 3,5-Di-tert-butyl-N-(2-chloro-4-nitro-phenyl)-2-hydroxy-benzamide or 3-tert-Butyl-N-(2-chloro-4-nitro-phenyl)-2-hydroxy-5-methyl-benzamide;
or a pharmaceutically acceptable salt or solvate thereof.
2. A compound according to claim 1, wherein m is 0.
3. A compound according to claim 1, wherein m is 1.
4. A compound according to claim 1, wherein m is 2.
5. A compound according to claim 1, wherein R1 represents phenyl, neopentyl, tert-butyl, isopropyl or 1,1-dimethylpropyl.
6. A compound according to claim 5, wherein R1 represents tert-butyl.
7. A compound according to claim 1, wherein R2 and R4 independently represent hydrogen or methyl.
8. A compound according to claim 1, wherein R3 represents $C_{1-6}$alkenyl or $C_{1-6}$alkynyl, both of which are optionally substituted.
9. A compound according to claim 8, wherein R3 represents styryl.
10. A compound according to claim 1, wherein R3 represents optionally substituted aryl.
11. A compound according to claim 10, wherein R3 is selected from phenyl, 4-cyano phenyl, 4-chloro phenyl, 4-nitro phenyl, 4-triflouromethyl phenyl, or radicals with the following structures

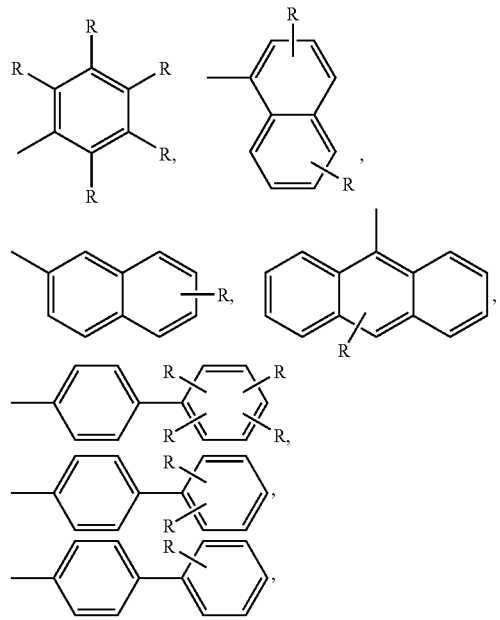

-continued

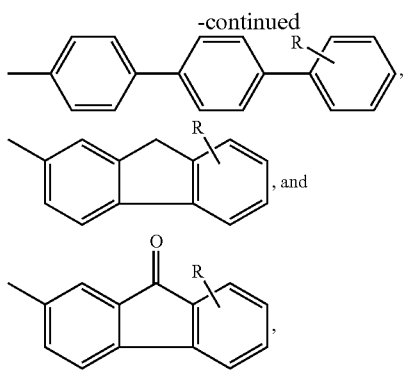

wherein R is selected from the list consisting of hydrogen, methyl, CF₃, Cl, Br, F, methoxy, ethoxy, methylcarbonyl, nitro, cyano, and phenyl, wherein said phenyl may optionally be substituted with Cl, Br, F, CF₃ or methoxy.

12. A compound according to claim 1, wherein R3 represents an optionally substituted heteroaryl.

13. A compound according to claim 12, wherein R3 is selected from

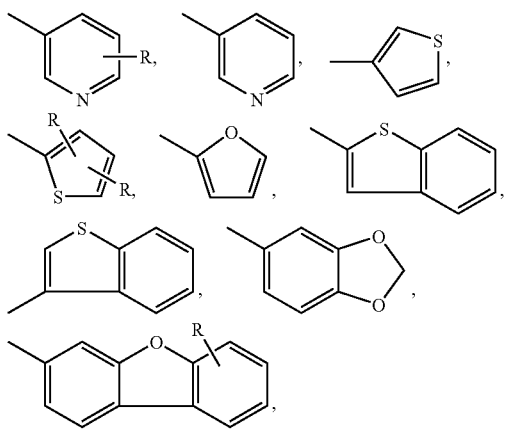

-continued

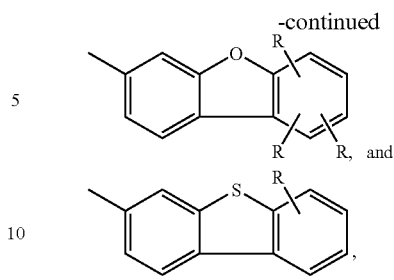

wherein R is selected from the list consisting of hydrogen, methyl, CF₃, Cl, Br, F, methoxy, ethoxy, methylcarbonyl, nitro, cyano, and phenyl, wherein said phenyl may optionally be substituted with Cl, Br, F, CF₃ or methoxy.

14. A compound according to claim 13, wherein R3 is selected from thiophen-2-yl, 5-cyano-thiophen-2-yl and benzo[b]thiophen-2-yl.

15. A compound according to claim 1 wherein R5, R6 and R7 together constitutes the substitution pattern 2-chloro-4-nitro or 2-trifluoromethoxy-4-nitro.

16. A compound according to claim 1 selected from the list consisting of 5-tert-Butyl-4-hydroxy-2-methyl-biphenyl-3-carboxylic acid (2-chloro-4-nitro-phenyl)-amide;

E) 3-tert-Butyl-N-(2-chloro-4-cyano-phenyl)-2-hydroxy-5-styryl-benzamide;

5-tert-Butyl-4-hydroxy-2-methyl-biphenyl-3-carboxylic acid (4-cyano-2-trifluoromethoxy -phenyl)-amide;

5-tert-Butyl-4'-cyano-4-hydroxy-2-methyl-biphenyl-3-carboxylic acid (4-cyano-2 -trifluoromethoxy-phenyl)-amide;

3-tert-Butyl-N-(2-chloro-4-cyano-phenyl)-5-(5-cyano-thiophen-2-yl)-2-hydroxy -benzamide; and 5-Benzo[b]thiophen-2-yl-3-tert-butyl-N-(2-chloro-4-cyano-phenyl)-2-hydroxy -benzamide.

17. A pharmaceutical composition comprising one or more compounds according to claim 1.

* * * * *

UNITED STATES PATENT AND TRADEMARK OFFICE
CERTIFICATE OF CORRECTION

PATENT NO. : 7,645,791 B2
APPLICATION NO. : 12/147678
DATED : January 12, 2010
INVENTOR(S) : Preben Houlberg Olesen et al.

It is certified that error appears in the above-identified patent and that said Letters Patent is hereby corrected as shown below:

In column 31, line 32, in claim 1, delete "-imidazolyl;" and insert -- -imidazolyl); --, therefor.

In column 33, line 25-30, in claim 13, delete " " and insert -- --, therefor.

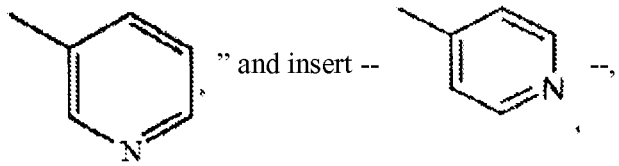

Signed and Sealed this

Twenty-third Day of November, 2010

David J. Kappos
*Director of the United States Patent and Trademark Office*